United States Patent [19]

Frazier

[11] Patent Number: 4,677,521
[45] Date of Patent: Jun. 30, 1987

[54] STATIC DISSIPATIVE GROUNDING STRAP

[76] Inventor: Thomas G. Frazier, c/o J. Penner Corporation, Waterside Industrial Park, Box B113, R.D. #2, New Hope, Pa. 18938

[21] Appl. No.: 865,069

[22] Filed: May 19, 1986

[51] Int. Cl.$^4$ ............................................. H05F 3/02
[52] U.S. Cl. ................................................. 361/220
[58] Field of Search .............. 361/232, 235, 212, 220, 361/223; 57/901

[56] References Cited

U.S. PATENT DOCUMENTS

| | | | |
|---|---|---|---|
| 4,398,277 | 8/1983 | Christiansen et al. | 361/220 |
| 4,459,633 | 7/1984 | Vandermark | 361/220 |
| 4,539,937 | 9/1985 | Workman | 361/232 X |
| 4,555,744 | 11/1985 | Maroney et al. | 361/212 |
| 4,577,256 | 3/1986 | Breidegam | 361/220 |
| 4,590,623 | 5/1986 | Kitchman | 57/901 X |

Primary Examiner—Donald A. Griffin
Attorney, Agent, or Firm—Z. T. Wobensmith, III

[57] ABSTRACT

A static dissipative device is disclosed for use by persons assembling, maintaining, repairing or operating sensitive electronic equipment. The static dissipative device includes a strap having a static dissipative layer in contact with the skin of the user, which layer consists of an electrically static dissipative material of high surface resistivity, and with an electrically conductive portion in contact with the static dissipative layer for connection to ground.

11 Claims, 13 Drawing Figures

STATIC DISSIPATIVE GROUNDING STRAP

BACKGROUND OF THE INVENTION

1. Field of the Invention The invention relates to an anti-static grounding device for use by persons assembling, maintaining, repairing or operating electronic equipment or the components thereof. In a preferred embodiment, the device comprises an anti-static wrist strap with attached wrist watch.

2. Description of the Prior Art

The sensitivity to static electricity of electronic equipment and its components, such as printed circuit boards, has increased considerably due to the decrease in the level of voltages required to operate printed circuit boards, which in some instances is in the amount of one volt. Printed circuit boards are expensive, and typically can cost in the range of $500.00 to $20,000.00 or more. In the manufacturing of such devices it is possible, through grounding mats and other precautions, to control the environment so as to reduce the exposure to static electricity and possible damage to the boards to an acceptable level. Such printed circuit boards and other sensitive equipment, after assembly, are typically packaged in an enclosure of anti-static material. When it is desired to replace a printed circuit board or other electronic component in the field, the repairman has to remove the component from its protective wrapping for installation into the equipment. It is difficult to control static electricity in the field working environment, and the charge carried or generated by the person installing the electronic components.

Various techniques have been utilized to attempt to alleviate damage to sensitive equipment or components due to the presence of static electricity. One method utilized in the prior art is to provide a grounded, conductive mat on the work surface, or on the floor. Another example of such a device is a touch bar device attached to the equipment which the operator touches before operating the equipment. A device of this type is disclosed in my co-pending application Ser. No. 735,870, now U.S. Pat. No. 4,586,106, issued Apr. 29, 1986.

While these devices are useful in controlled areas, it is often impractical to use them, and environmental conditions can exist that render them ineffective when handling sensitive electronic components.

It is also common to use a conductive wrist band to effectuate grounding of accumulated static electricity from a person assembling, maintaining, repairing or operating electronic equipment. The wrist strap is commonly worn by the person involved with the equipment, and is usually put on prior to such involvement.

It has been recognized that a conductive wrist band attached to ground can present a hazard due to an electrical short occurring in the ground circuit, thereby presenting a shock or electrocution hazard to the wearer, and various devices have been developed with safety features to attempt to alleviate these dangers.

Conductive wrist band devices are normally connected to ground by way of a grounding cord. As a safety feature, an inline resistor may be included in the cord or in the device itself to protect the wearer from high voltage conditions, which may exist when the grounding cord is disconnected from the device (and the conductive element is exposed to possible high voltage electrical circuits) or when the cord itself is accidentally connected to a high voltage source, or an electrical fault exists in the circuit to which the ground is connected.

Prior art wrist devices are typically constructed of a conductive material that is placed into electrical contact with the skin of the person wearing the device. The conductive material may take the form of a metallic plate on the inside of a wrist band, and may be a carbon-loaded conductive plastic or carbon-loaded conductive fabric. The prior art device of one popular wrist strap is of open mesh elastic woven fabric, with an electrically conductive plate in contact with the wearers skin, attached to a layer of fabric, with conductive metallic threads, a rivet in contact with the plate passing through the fabric, with an insulative plate on the outside of the strap, and with an outer exposed stud engaged with the rivet. Such devices rely on the wrist strap having an outer surface that is insulated from the conductive inner surface.

These prior art devices that rely on an electrically conductive material in contact with the skin, usually specify a conductive material having a surface resistivity below 100,000 ohms per square.

The Vandermark U.S. Pat. No. 4,459,663 describes a typical wrist device for draining off static electricity, which comprises an electrically conductive inner surface and an electrically insulated outer layer. Electrical contact to the skin of the user is made by a conductive metallic plate on the inside surface of the device. The electricity is then passed through an inline resistor, packaged within a casing, and to an exposed conductive eyelet portion in a dielectric cover on the case. The conductive eyelet portion may be attached to ground by the connection of a suitable grounding cord. This device is not entirely satisfactory, in that the inline resistor, of conventional form, which is included inside the casing, is costly, leads to an increase in the bulk and size of the device and is readily subject to contamination. It is also undesirable, as described in the Vandermark patent, to provide a case made of two dissimilar materials to encapsulate a conventional resistor. This component case can allow contaminating substances (water, perspiration, etc.) to enter the case, shorting out the resistor and destroying the usefulness of the resistor and thereby exposing the user to possible electrical shock.

In addition, metal conductive plates are uncomfortable and because of their rigidity, can separate from time to time from the skin resulting in intermittent static grounding. This type of device is often not worn by the user because of its bulk, and the potential safety hazards that can develop.

The U.S. Patent to Christiansen, et al. U.S. Pat. No. 4,398,227 describes a conductive elastomeric fabric and body strap. The device is formed of an insulative and elastomeric yarn, which is formed into interlocking loops on both the inner and outer surfaces. The device is applied by slipping it over the wrist, and due to its elastomeric properties, it conforms to the shape of the wrist of the wearer. The device, unfortunately, lacks the necessary safety features to protect the wearer from shock in the case of electrical fault, which could result when the yarn becomes wet or soaked with perspiration, which would cause its insulative qualities to disappear, and a potentially dangerous condition could result.

For a static grounding wrist band to function optimally, it should have the following characteristics:

It should be attractive and easily worn to induce the user to wear it at all times when working on static sensitive components.

It should make proper electrical connection between the wrist and the ground cord, particularly at the point of interface between the skin and the inside of the strap. The better this electrical interface, the better and more efficacious the grounding strap will be.

Total resistance between the wrist and the grounding portion of the wrist strap should not exceed (typically) 10 megohms as measured with a bias voltage of at least 10 volts. This resistance of 10 megohms or less will allow static generated charges (either generated through triboelectric forces or through changes in the wearer's capacitance [transient voltage]) to drain to ground in less than 0.04 seconds, a typically safe drain time to prevent the accumulation of static charges on the wearer.

The wrist strap should present no direct electrical contact with the skin either when the ground cord is attached or detached to prevent accidental shock or electrocution to the wearer if the conductive portion were to come in contact with high electrical voltages. Ideally, an in-line resistance of at least 0.25 megohms or higher should be included to assure protection against accidental shock.

During use of any of the prior art wrist straps, the user is instructed to first remove any wrist watch that he or she may be wearing, as the watch may have an unsafe conductive band or case. This is an inconvenience to persons who need to know the time and/or prefer to wear a watch at all times, and often results in those persons failing to utilize a static-draining wrist strap, and causing resultant damage to the electronic equipment. The prior art does not disclose, and it has not heretofore been proposed, to provide a static dissipative grounding strap, which may be attached to a wrist watch which has and must have, for safety reasons, a protective resistive element between the skin and an exposed conductive snap when worn under diverse working and living conditions, and when the ground cord is unconnected. The prior art also does not provide for an adapter kit for converting a conventional wrist watch into a static grounding device for use by persons who wish to wear their own personal wrist watch while involved with electrically sensitive equipment.

SUMMARY OF THE INVENTION

The invention comprises a static draining device for draining static electricity from the body of a person to ground. The device is in the form of a wrist band to be worn by a person, and comprises a flexible dielectric strap portion adapted to be worn on the wrist, a static dissipative layer, preferably non-porous in construction, adjacent to the inside of the strap to contact the skin of the wearer, and an electrically conductive snap portion, which extends through the dielectric strap portion, and is in electrical contact with the static dissipative layer, and may be connected to a ground cord. The static dissipative strip may include a dielectric strip with a layer of an electrically static dissipative material having a typical exposed surface resistivity between one and 10 megohms to the ground snap. Resistivity ranges as low as 0.250 megohms and as high as 200 megohms may also be considered safe for use under certain circumstances. The low resistance protects the wearer from accidental high voltage shock if the exposed conductive snap accidentally comes in contact with high voltage current.

The high resistive limit is determined by the maximum static electricity drain time permitted by the static sensitive components being handled. Within these suggested ranges of resistivity, drain times of the static charge generated will be drained to zero potential in 0.04 seconds or less, well within the safe limit ranges of most static sensitive electrical components.

In an additional embodiment of the invention, an electrically safe wrist watch is incorporated into the dielectric strap portion worn by the user. The watch casing is also preferably formed from a dielectric material. With this embodiment, it is not necessary for a person to wear an unsafe watch and hence the person does not have to bother removing the unsafe watch prior to the use of the static draining device.

In yet another embodiment of the invention, a kit is provided for adapting a conventional wrist watch to a static draining device with an adaptor kit which consists of a flexible dielectric strap having a buckle or Velcro ® strips on the ends, and a static dissipative strip on the inside of the strap, which are attached to the wrist watch of the user on the inside with a snap portion on the outside in contact with the static dissipative strip, which may be connected to ground.

The principal object of the invention is to provide a static draining device that is safe and efficacious while used under diverse operating conditions and is useful for a variety of applications.

A further object of the invention is to provide a static draining device that improves the electrical connection at the point of interface between the wearer's skin and the device by providing an extended, flexible, non-porous strip of static dissipative material for contact with the skin of the wearer. This feature assures sufficient body moisture to build up and remain under the strip, to improve the electrical contact at the interface and to assure intimate electrical contact between the device and the skin.

Other objects and advantageous features of the invention will be apparent from the description and claims.

DESCRIPTION OF THE DRAWINGS

The nature and characteristic features of the invention will be more readily understood from the following description taken in connection with the accompanying drawings forming part hereof in which.

Figure 1:
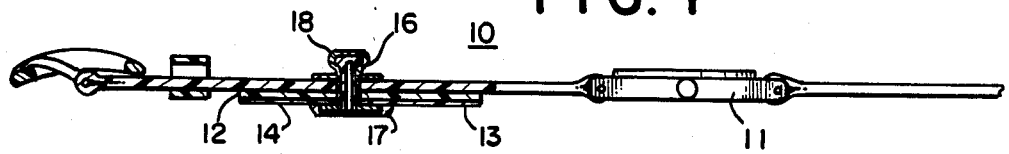
FIG 1 is a side elevational view in partial section, of one embodiment of the device of the invention which embodiment includes a wrist watch with a dielectric outer case.

It should, of course, be understood that the description and drawings herein are illustrative merely and that various modifications and changes can be made in the structures disclosed without departing from the spirit of the invention.

DESCRIPTION OF THE PREFERRED EMBODIMENTS

An important feature of the invention is the use of a static dissipative layer (as distinguished from a conductive layer) in intimate contact with the skin of the person wearing the device. As is noted in the prior art, the typical prior art static draining wrist device employs a conductive material, which usually has a surface resistivity of less than 100,000 ohms per square. In contrast, the device of the invention includes a static dissipative layer in direct contact with the skin of the user, which layer in the preferred embodiment consists of a flexible, static dissipative polymer material having an exposed surface resistivity to a grounded snap portion, of typically between one and 10 megohms. The use of this material in place of a conductive material also obviates the need to include a conventional and bulky inline resistor in the path between skin contact and ground. The safety of the user is thereby ensured due to the resistive nature of the static dissipative strip, and without the addition of an extraneous conventiona resistor.

Referring now more particularly to the drawings and FIGS. 1, 2, 3, 8 and 9 thereof, one embodiment of the invention consists of a flexible dielectric strap 10 formed of any suitable well known dielectric material and adapted to be worn on the wrist of user (not shown). The strap 10 may optionally include a wrist watch 11 of conventional well known type. If a wrist watch is provided, however, it is preferable that all exposed portions of the watch surface be formed of a dielectric insulative material, e.g., plastic resin. The flexible dielectric strap 10 has a dielectric strip 12 thereon and in the preferred embodiment is non-porous, and located on the inside face of the strap 10 in order to be in intimate contact with the skin of the person (not shown) wearing the device. The strip 12 may extend any desired length along the inside face of the strap 10, consistent with the desired static dissipative requirements and even over the rear face of the watch 11. Due to the flexible nature of the strip 12, the strip may be formed to any desired length without discomfort to the user and remains in intimate skin contact due to its conformity to the skin surface. The longer the strip therefore, the greater skin contact and the greater the functionality of the device.

The strip 12 is provided with a static dissipative layer 13, which may consist of a polymer which has been rendered electrically conductive by the additon of activated carbon black or other suitable materials. various polyesters and vinyl acrylic materials are suitable vehicles for activated carbon black, as is well known in the art. It has been found to be particularly desirable to form the static dissipative layer by depositing an electrically conductive ink upon a textured flexible substrate layer (including polycarbonate or polyvinylchloride), such as by the silk screen process. A preferred ink consists of polymethacrylate of vinyl/acrylic, containing carbon black, in a slow drying solvent. The methacrylate may be deposited as a monomer, and allowed to cure on the surface of the substrate layer, such as strip 12. The preparation and electrical characteristics of the static dissipative strip layer are more fully described in my co-pending application Ser. No. 735,870.

The static dissipative layer 13 may be applied to the strip 12 or directly to the back of flexible strap 10, if desired, and additionally, may be provided with a non-porous flexible coating 14, such as Teflon ® or other suitable material with low surface tension characteristics, so that the build-up of dirt, waxes, or other contaminants can be avoided thereby reducing the chance of increased surface resistivity due to contaminant build up.

The static dissipative layer 13 is electrically connected to a conductive ground cord connector snap 16 through an opening in the dielectric strip 12 and the strap 10 with a metallic grommet end 15 of the snap 16 in contact with the static dissipative layer 13. A closed end dielectric rivet 17 is engaged in the exposed open end of the connector snap 16 to provide intimate sealing contact with the layer 13, and at the same time to insulate all portions of the conductive end 15 from direct contact with the wearer's skin. This sealing feature prevents perspiration and other contaminants from contact with grommet end 15, and shorting out the safety resistive feature of the static dissipative layer 13.

The inclusion of a non-porous flexible static dissipative strip 12 with a static dissipative layer 13 as the primary means of making skin contact is a substantial feature of the invention and a dramatic improvement over the prior art. In the prior art, as has been discussed, the wearing of the device, particularly in conjunction with a wrist watch would expose its components to perspiration which can short out a conventional resistor and make the device unsafe. In the present device, perspiration is prevented from shorting out or otherwise destroying the desired electrical resistance while at the same time improving electrical contact at the critical interface between the skin of the wearer, and the static dissipative layer of the device.

In use, electrical contact is made between the static dissipative layer 13 and the conductive snap rivet 16. The electrical charge, which is accumulated on the static dissipative layer 13, is transferred to and collected at the conductive snap rivet 16, to be transferred to an attachment to ground such as by an electrical cord 17', having a complementary female conductive snap 17A for attachment to the head 18 of the male snap rivet 16. The snap 17A is attached to a length of electrical wire 20 which may be attached directly to ground by an alligator clip 21. Accordingly, when the device 10 is to used, the person wearing the device has only to connect the female snap portion 17A to achieve proper ground. When the device is not in use, the ground wire 17' can be easily removed. In the embodiment described above, in which a wrist watch 11 is included as part of the device, the person may wear the device for everyday use, and has only to connect the device to ground, when arriving at the work location, by attachment of the female snap portion 17A, without the necessity of removing his or her personal watch and applying a separate wrist strap device.

It is also important to note that the static dissipative layer 13 of the invention prevents the exposed head 18 of the snap 16 from presenting a hazardous condition to the user when the device is not connected to ground.

This safety feature occurs because the static dissipative layer 13 is of a sufficiently high resistance that there is no need to install a separate conventional resistor to protect the user from electrical shock, should the head 18 come into contact with a source of electrical energy.

Figure 4:
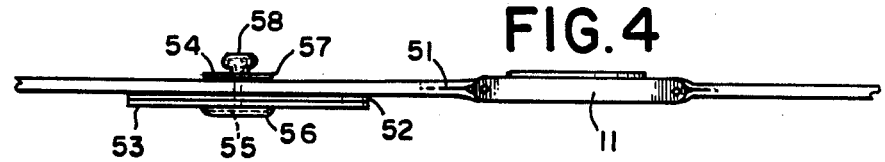
FIG. 4 is a side elevational view, similar to FIG. 1, but of another embodiment of the device.

Referring now to FIG. 4, another embodiment of the device 50 of the invention is illustrated which includes a watch 11, and a flexible dielectric strap 51 similar to strap 10, with a dielectric strip 52 on the inside face of the strap 51 and with a static dissipative layer 53 thereon similar to layer 13, for intimate skin contact. A rivet 54, similar to rivet 16, is provided with a metal grommet end 55 in direct contact with the static dissipative layer 53 and with a dielectric patch 56 of well known type covering the exposed grommet end 55 in sealing relationship with the layer 53.

Figure 9:
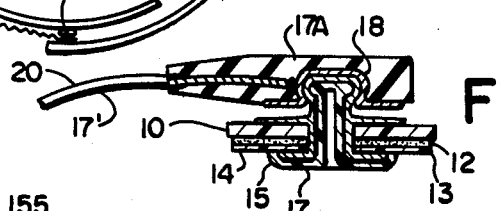
FIG. 9 is a fragmentary partial vertical sectional view, taken approximately on the line 9—9 of FIG. 8.
Figure 8:
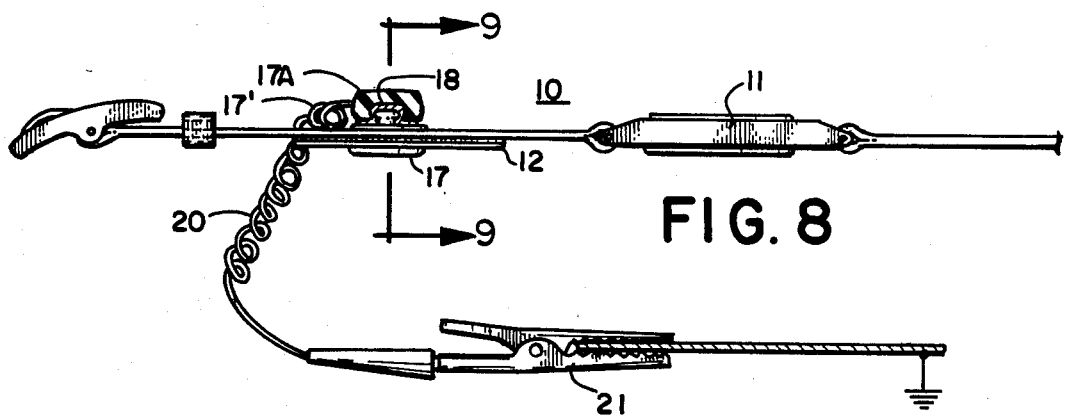
FIG. 8 is a side elevational view of the device of FIG. 1 in partial section, and shown with an attached grounding cord.

The rivet 54 has a plate 57 in contact with the outer face of the strap 51 and a head 58 which may be connected to ground by a ground cord 17' of FIGS. 8 and 9.

In another embodiment of the invention to be described, an adaptor kit is provided for adapting a conventional wrist watch to be a static dissipative device. The adaptor kit includes a dielectric strap with a backing strip, which serves as a substrate for a static dissipative layer for intimate skin contact. The device may be looped around or attached directly to the band of a conventional wrist watch, so that the static dissipative portion of the strip of the person wearing the watch is maintained in electrical contact with the skin.

Figure 5:
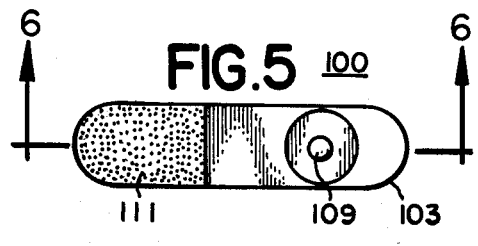
FIG. 5 is a top plan view of another embodiment of the device of the invention.
Figure 6:
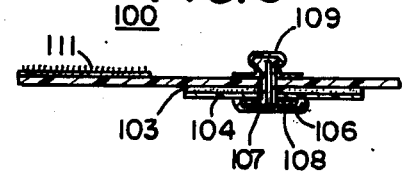
FIG. 6 is a vertical sectional view taken approximately on the line 6—6 of FIG. 5.
Figure 7:
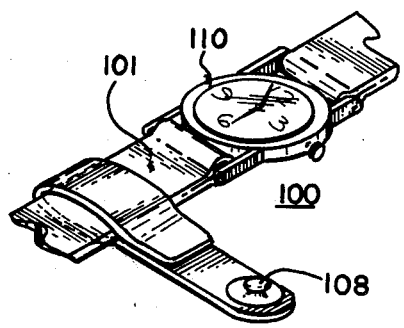
FIG. 7 is a view in perspective of a watch and band with the component of FIG. 5 attached thereto.

Referring now to FIGS. 5, 6 and 7, one embodiment of adaptor kit 100 is shown wherein a conventional wrist watch 110 having a band 101 is fitted with the adaptor kit. The adaptor kit includes a flexible dielectric strap 102 with an attached flexible backing strip 103, with a static dissipative layer 104 on the surface thereof for skin contact, as described for FIGS. 1 and 3.

In this embodiment, the strap 102 of the device 100 is provided with a layer 111 of pressure sensitive adhesive of well known type, enabling the adaptor device to be wrapped around the entire watch band 101. Accordingly, when the watch is worn, the static dissipative layer 104 is maintained in intimate contact with the user's skin (not shown).

A rivet 106 is provided, similar to rivet 16 above, with a grommet end 107 in contact with layer 104 and has a plastic rivet 108 engaged thereon for sealing of rivet 106 from perspiration, as described for rivet 17. The rivet 106 is additionally provided with a head 109 for connection to a grounding cord (not shown) as described for cord 17' above.

The device 100 may be attached to the wrist watch 110 by any suitable means, so long as the static dissipative layer 104 is maintained against the skin of the user (not shown) when the watch is worn.

Figure 10:
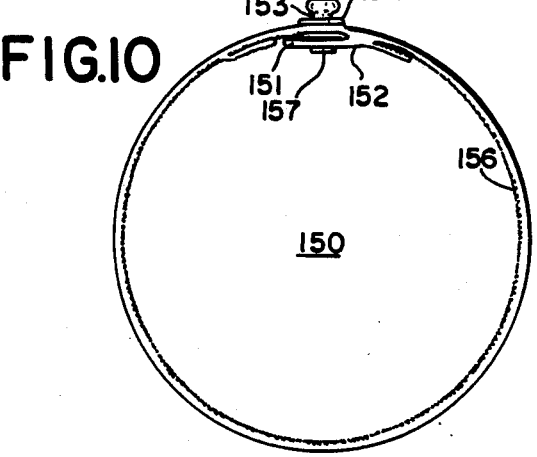
FIG. 10 is a side elevational view of another embodiment of the static dissipative grounding strap device of the invention.

Referring now to FIG. 10, another embodiment of static dissipative grounding device is illustrated which includes a stretch band 150 adapted to be worn on the wrist of the user (not shown) with a strip 151 of dielectric material thereon, which has a layer of static dissipative material 152 thereon, as described above for layer 13, with a rivet 153 in contact therewith, and extending upwardly through the band 150. A plate 154 is provided in contact with the outer face of the band 150, and with a head 155 of rivet 153 in contact therewith, which head may be connected to a suitable grounding cord (not shown) such as cord 17'. A plastic rivet 157 is provided engaged in rivet 153 as described for rivet 17. The embodiment illustrated in FIG. 10 is provided with an inner occlusive coating or layer 156 of latex or other suitable occlusive coatings to make the band 150 impervious to water and perspiration to thereby maintain the band as an insulative layer, with electrical contact only through the rivet 153.

Figure 11:
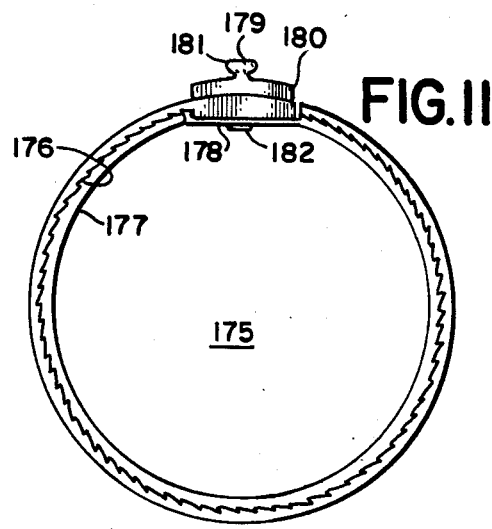
FIG. 11 is a view similar to FIG. 10, illustrating another embodiment of the device of the invention.

Referring now to FIG. 11, another embodiment of static dissipative grounding device 175 is illustrated which includes a band 176 of plastic, such as pleated PvC or flat ribbon elastic, being non-porous and having an outer elastic tubular band 177 engaged therewith. A layer of static dissipative material 178 is provided on the inside of band 177, for contact with the skin of the user (not shown), with a rivet 179 engaged therewith extending through the bands 176 and 177, with a plate 180 in contact with the outer face of band 176 and with a head 181 for engagement by a ground cord (not shown) such as ground cord 17'. A plastic rivet 182 is provided, similar to rivet 17, and engaged in rivet 179 for sealing as described for FIGS. 1, 2 and 3.

Figure 2:
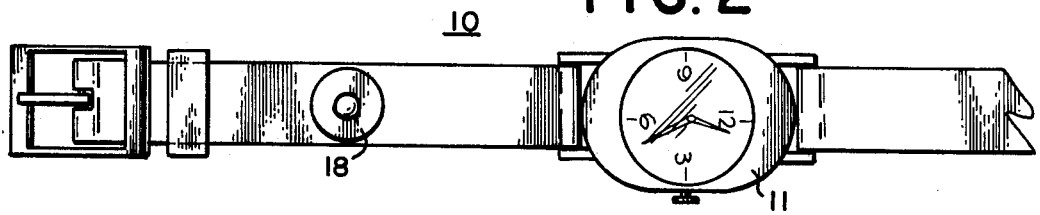
FIG. 2 is a top plan view of the device of FIG. 1.
Figure 3:
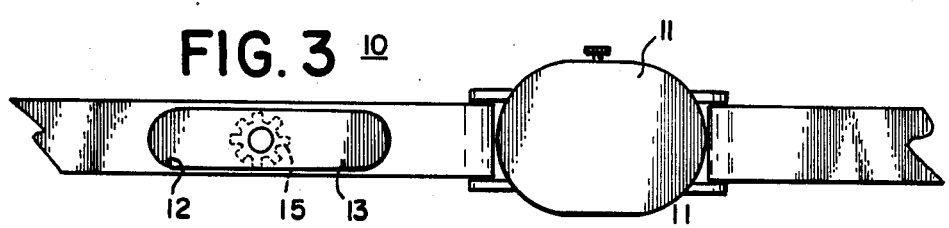
FIG. 3 is a bottom plan view of the device of FIG. 1.
Figure 12:
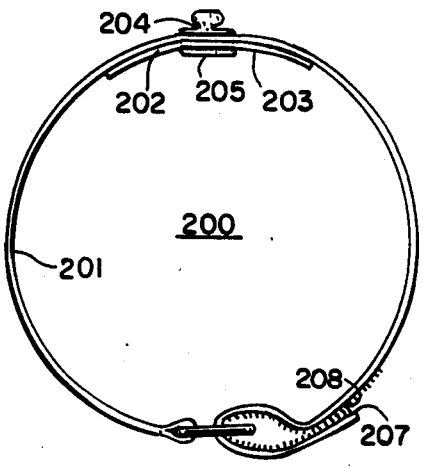
FIG. 12 is a view similar to FIG. 10, illustrating another of the device of the invention.

Referring now to FIG. 12, another embodiment of static dissipative grounding device 200 is illustrated, which includes a band 201 of non-porous dielectric material, similar to strap 10 of FIGS. 1, 2 and 3, and with a strip of dielectric material 202 on the inner face which has a layer 203 of static dissipative material similar to layer 13 for contact with the skin of the user (not shown), and with a rivet 204 extending through the band 201 as described for device 175. In addition, a plastic sealing rivet 205 is engaged in rivet 204 as described for rivet 17. The band 201 at one of its ends is provided with a buckle 206 of conventional type, which can be of resin plastic and which band 201 also has a strip of Velcro ® 207 thereon so that the end can be threaded through buckle 206 and engaged with a complimentary strip of Velcro ® 208, to provide for adjustment of the device 200 to fit varying size wrists. The device 200 is designed so as not to expose any porous section of the fastening buckle to direct contact with the skin. This prevents perspiration from providing a direct electrical contact to the skin.

Figure 13:
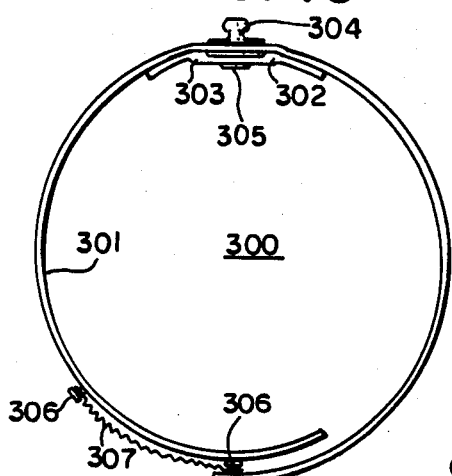
FIG. 13 is a view similar to FIG. 10 showing still another embodiment of the device of the invention.

Referring now to FIG. 13, still another embodiment of static dissipative grounding device 300 is provided, which includes a non-porous dielectric band 301, similar to band 201 with a strip of dielectric material 302 on the inside face, which has a layer of static dissipative material 303 on the inside of the strip 302 for intimate contact with the skin of the user (not shown), is provided with a contact rivet 304 and a sealing rivet 305 as described for device 200 above.

The band 301, at its ends, is provided with plastic rivets 306 which are each engaged with the ends of an elastic material 307 urging the ends together and providing for retention of the band 301 on the wrist of the user (not shown).

It should be noted that for the various static dissipative straps described above, that the electrical characteristics are such that from any point on the static dissipative layer to the electrical contact on the outer part of the band, the resistance between the point and the contact is never, typically, less than one ohm or more than 10 ohms.

It will, of course, be appreciated that any suitable means of attaching the adapter kit strip to the watch band, for example a hook and loop fastener, may be employed in lieu of the disclosed embodiments.

It will thus be seen that a static dissipative grounding strap has been described with which the objects of the invention are achieved.

I claim:

1. A device to be worn on the wrist for draining static electricity from a person to ground which comprises
    a flexible dielectric strap portion to be worn on the wrist of said person;
    static dissipative means adjacent said strap portion for contact with the skin of said person;
    an electrically conductive portion in electrical contact with said static dissipative means;
    said static dissipative means having a surface resistivity such that the resistance between any point on the static dissipative means and the electrically conductive portion is in the range of 0.25 to 200 megohms; and
    insulating means for insulating the electrically conductive portion from contact with the skin of said person.

2. A device as defined in claim 1 in which
said strap portion is non-porous.

3. A device as defined in claim 1 in which
said static dissipative means includes a flexible dielectric strip portion adjacent said strap portion; and
said strip has a layer of electrically static dissipative polymer material thereon for contact with the skin of said person.

4. A device as defined in claim 3 in which
an additional non porous layer of low surface tension material is provided on top of said static dissipative layer to prevent the build up of contaminants.

5. A device as defined in claim 1 in which
said static dissipative means includes a layer of electrically static dissipative polymer material on said dielectric strap adjacent said skin of said person for intimate electrical contact with said person.

6. The device as described in claim 1 wherein
said flexible dielectric strap has a wrist watch attached thereto.

7. The device as described in claim 6 wherein
all exposed portions of said wrist watch are formed of a dielectric material.

8. The device as described in claim 1 wherein
means are provided for attaching said conductive portion to ground.

9. An adaptor strap for attachment to a wrist watch for draining static electricity from a person to ground comprising
    a flexible dielectric strip;
    a static dissipative layer on said strip for contact with the skin of said person;
    said static dissipative material consisting of a static dissipative polymer material having a surface resistivity between 0.25 and 200 megohms;
    means for attaching said strap to a wrist watch such that the static dissipative layer is maintained in contact with the skin of said person;
    an electrically conductive portion in electrical contact with said static dissipative layer; and
    insulating means for insulating the electrical conductive portion from the skin of said person.

10. The adaptor strap set forth in claim 9 wherein
said attaching means consists of pressure sensitive adhesive on said strip.

11. The adaptor strap set forth in claim 9 wherein
means are provided for attaching said conductive portion to ground.

* * * * *